United States Patent
Horvath

(10) Patent No.: US 9,358,043 B2
(45) Date of Patent: Jun. 7, 2016

(54) DISTRACTION MEMBRANE

(75) Inventor: Domonkos Horvath, Jestetten (DE)

(73) Assignee: Celgen AG, Zug (CH)

( * ) Notice: Subject to any disclaimer, the term of this patent is extended or adjusted under 35 U.S.C. 154(b) by 310 days.

(21) Appl. No.: 13/992,366

(22) PCT Filed: Dec. 7, 2011

(86) PCT No.: PCT/EP2011/006134
§ 371 (c)(1),
(2), (4) Date: Jun. 7, 2013

(87) PCT Pub. No.: WO2012/076161
PCT Pub. Date: Jun. 14, 2012

(65) Prior Publication Data
US 2013/0274819 A1    Oct. 17, 2013

(30) Foreign Application Priority Data
Dec. 10, 2010 (DE) .......................... 10 2010 055 432

(51) Int. Cl.
| | |
|---|---|
| A61F 2/46 | (2006.01) |
| A61B 17/68 | (2006.01) |
| A61B 17/66 | (2006.01) |
| A61B 17/80 | (2006.01) |
| A61C 8/02 | (2006.01) |
| A61F 2/28 | (2006.01) |
| A61F 2/30 | (2006.01) |

(52) U.S. Cl.
CPC .............. *A61B 17/68* (2013.01); *A61B 17/666* (2013.01); *A61B 17/8071* (2013.01); *A61C 8/0006* (2013.01); *A61F 2/28* (2013.01); *A61F 2/2803* (2013.01); *A61F 2/2846* (2013.01); *A61F 2002/3025* (2013.01); *A61F 2002/30062* (2013.01); *A61F 2002/30112* (2013.01); *A61F 2002/30237* (2013.01); *A61F 2002/30245* (2013.01); *A61F 2002/30507* (2013.01); *A61F 2002/30525* (2013.01); *A61F 2002/30784* (2013.01); *A61F 2310/00023* (2013.01)

(58) Field of Classification Search
CPC ........... A61B 17/8061; A61B 17/8071; A61B 17/8085; A61B 17/663; A61B 17/666; A61F 2/2846; A61F 2/2803
See application file for complete search history.

(56) References Cited

U.S. PATENT DOCUMENTS

| | | | | |
|---|---|---|---|---|
| 5,769,637 | A | * | 6/1998 | Morgan ............. A61B 17/8071 433/176 |
| 5,980,252 | A | * | 11/1999 | Samchukov et al. ......... 433/215 |
| 6,712,851 | B1 | | 3/2004 | Lemperle et al. |
| 2005/0074437 | A1 | * | 4/2005 | Horvath ............... A61C 8/0006 424/93.7 |
| 2005/0159755 | A1 | * | 7/2005 | Odrich ................... A61B 17/66 606/86 R |
| 2007/0269769 | A1 | | 11/2007 | Marchesi |
| 2010/0266979 | A1 | | 10/2010 | Karmon |

FOREIGN PATENT DOCUMENTS

| | | |
|---|---|---|
| DE | 42 32 511 | 3/1994 |
| FR | 2 713 090 | 6/1995 |
| JP | 2-82964 | 3/1990 |

(Continued)

*Primary Examiner* — Christopher Beccia
*Assistant Examiner* — Diana S Jones
(74) *Attorney, Agent, or Firm* — Jordan and Hamburg LLP

(57) ABSTRACT

The present invention relates to an arched membrane and/or a membrane having rounded edges for regenerating a bone, in particular a distraction membrane, suitable for callus distraction, notably in the jaw region, to the use of the membrane for callus distraction, and to methods for callus distraction.

24 Claims, 12 Drawing Sheets

(56) References Cited

FOREIGN PATENT DOCUMENTS

| JP | 11-262491 | 9/1999 |
| JP | 2003-25241 | 1/2003 |
| JP | 2003-269260 | 9/2003 |
| WO | WO-01/91663 | 12/2001 |
| WO | WO-2008/047415 | 6/2013 |

* cited by examiner

DISTRACTION MEMBRANE

BACKGROUND OF THE INVENTION

The present invention relates to a membrane for regenerating a bone, in particular a distraction membrane, suitable for callus distraction, notably in the jaw region, to the use of the membrane for callus distraction, and to methods for callus distraction.

Bone losses are currently generally filled with bone substitute material or with autogenous or allogenic bone.

From a biological view, an autologous spongiosa transplant is the best substitute material for bone. However, such transplants are only available to a limited extent and exhibit a high resorption rate after transplantation.

The materials and techniques employed in the prior art frequently provide inadequate bone quality, so that implants, for example, are not rigidly anchored in the beds. Additionally, the bone substitute is frequently not sufficiently vascularized, and as a result the risk of infection is increased. Methods according to the prior art often also employ growth factors, which significantly increase the costs of the procedures.

Instead of using a bone substitute, lacking bone substance can also be partially filled in by way of bone regeneration. Segmental osseous discontinuity on long bones can thus be treated by way of distraction osteogenesis.

Callus distraction has been known for more than one hundred years. The most important biological stimulus for osteogenesis is mechanical stress. Piezoelectrical forces are released in the process, which activate osteoblasts and osteoclasts. Distraction osteogenesis induces new bone formation by triggering biological growth stimuli by slowly separating bone segments. This method achieves the direct formation of woven bone by way of distraction. Defined tensile stress during bone generation is essential. If such defined tensile stress is applied to bone fragments, the mesenchymal tissues in the gap and on the adjoining fragment ends show osteogenetic capacity. If sufficient vascular potency exists, progressive distraction results in metaplasia of the organized hematoma, also referred to as a blood clot, in a zone of longitudinally arranged, fibrous tissue, which under optimal external and internal conditions can convert directly into woven bone. However, an aggravating factor is that the bone tissue is subject to highly complex control during regeneration.

WO 01/91663 A1 and U.S. Pat. No. 5,980,252 describe devices and methods for callus distraction by way of artificial interfaces, for example membranes. The membranes used there are flat plates or flat small plates, which are usually made of metal, for example titanium. When these plates or small plates are moved for distraction of the bone, the edges and the lateral faces thereof, which form the height of the membrane, graze the neighboring tissue. This results in irritation and further injury of the neighboring tissue, whereby healing may be worsened.

In addition, these flat plates can only be used to distract smaller regions of a bone section that is not planar, which is to say flat, for example of a jaw, because otherwise the membrane is not evenly seated against the bone.

SUMMARY OF THE INVENTION

The technical problem underlying the present invention is to provide a membrane that makes it possible to carry out bone regeneration methods that overcome the drawbacks of the prior art.

The technical problem underlying the present invention is also to provide membranes, uses thereof and methods that make it possible to regenerate bone, and in particular regenerate bone by way of distraction, wherein the tissue adjoining the membrane is irritated less or injured less than by membranes from the prior art, or is not irritated or injured at all.

The technical problem underlying the present invention is also to provide membranes, uses thereof, and methods that make it possible to regenerate non-planar bone sections, for example an alveolar ridge.

The present invention solves the underlying technical problem in particular by providing membranes, and in particular distraction membranes, methods and uses.

The present invention solves the underlying technical problem in particular by providing a membrane, also referred to as a distraction membrane, which is suitable for callus distraction, especially in the jaw region, wherein the membrane comprises a contact surface and a counter-surface, and wherein at least a sub-region of the contact surface and a sub-region of the counter-surface are arched. The membrane is thus arched over at least a portion of the length or width of the membrane.

The present invention also solves the underlying technical problem by providing a membrane, also referred to as a distraction membrane, which is suitable for callus distraction, especially in the jaw region, wherein the membrane comprises a contact surface, a counter-surface and at least one lateral face, and wherein the edges between the contact surface and the at least one lateral face and/or between the counter-surface and the at least one lateral face are rounded.

The present invention also solves the underlying technical problem by providing a distraction membrane suitable for bone distraction in the jaw region, wherein the distraction membrane comprises a contact surface, which is used for osteoblasts to line or adhere to in the region of a bone defect, a counter-surface located opposite the contact surface, and at least one lateral face, and wherein at least a sub-region of the contact surface and a sub-region of the counter-surface are arched, wherein all edges between the contact surface and the at least one lateral face and between the counter-surface and the at least one lateral face are rounded.

The present invention also solves the underlying technical problem by providing a distraction membrane suitable for bone distraction in the jaw region, wherein the distraction membrane comprises a contact surface, which is used for osteoblasts to line or adhere to in the region of a bone defect, a counter-surface located opposite the contact surface, and at least one lateral face, and wherein at least a sub-region of the contact surface and a sub-region of the counter-surface are arched, wherein the distraction membrane has rounded edges, wherein all edges between the contact surface and the at least one lateral face and between the counter-surface and the at least one lateral face are rounded.

A preferred embodiment is a membrane, also referred to as a distraction membrane, that is suitable for callus distraction, especially in the jaw region, wherein the membrane is arched according to the invention, and wherein the membrane comprises a contact surface, a counter-surface and at least one lateral face, and wherein the edges between the contact surface and the at least one lateral face and/or between the counter-surface and the at least one lateral face are rounded.

The present invention also solves the underlying technical problem by providing a membrane, also referred to as a distraction membrane, which is suitable for callus distraction, especially in the jaw region, wherein the membrane comprises a contact surface, a counter-surface, and at least one lateral face, and wherein the at least one lateral face is bent, in particular bent toward the contact surface.

A preferred embodiment is a membrane, also referred to as a distraction membrane, that is suitable for callus distraction, especially in the jaw region, wherein the membrane according to the invention is arched, and wherein the membrane comprises a contact surface, a counter-surface and at least one lateral face, and wherein the at least one lateral face is bent, in particular bent toward the contact surface.

In the context of the present invention, a membrane is understood to mean a medical membrane, which is suitable for the distraction of a bone, preferably of a jaw bone, especially in the dental field. Such a membrane is also referred to as a distraction membrane.

The present teaching includes, in particular membranes, distraction devices and methods for bone regeneration, wherein preferably bones in the jaw region and/or in the periodontal region are to be regenerated.

In the present invention, the term 'bone regenerations' in particular is understood to also mean the regeneration of bone defects, for example after cystectomy, tumor surgery or trauma surgery or the like, regardless of the topography, and/or in particular also the regeneration of smaller bone defects caused by periodontitis, for example.

In the context of the present invention, a membrane is understood to mean a body that is plate-shaped, which is to say planar or flat, in the non-arched state. The membrane has a contact surface, which is used for osteoblasts to line or adhere to in the region of a bone defect, and a counter-surface located opposite the contact surface. These two surfaces can take on any shape, for example they can be round, oval, quadrangular or polygonal. The contact surface and the counter-surface of the membrane are preferably rectangular in the non-arched state. In the non-arched state, the sizes of these two surfaces in a rectangular membrane result from the length and width of the membrane. The membrane additionally has at least one lateral face, and more particularly four lateral faces if it is a rectangular membrane. In the non-arched state, the sizes of two of the lateral faces result from the height and the length of a rectangular membrane, and the sizes of the two remaining lateral faces result from the height and width of the membrane. According to the invention, the membrane is as thin as possible, which means that the sizes of the lateral faces are several times smaller than the size of the contact surface, and in the case of a quadrangular membrane, the height of the membrane is several times smaller than the length and the width of the membrane.

In the context of the present invention, a membrane is preferably a distraction membrane.

A distraction membrane, which is suitable for bone distraction in the jaw region, is preferred, wherein the membrane comprises a contact surface and a counter-surface, and wherein at least a sub-region of the contact surface and a sub-region of the counter-surface are arched, and wherein the membrane has rounded edges.

A membrane that comprises a contact surface, a counter-surface and at least one lateral face is preferred, wherein at least one sub-region of the contact surface and a sub-region of the counter-surface are arched, and wherein the edges between the contact surface and the at least one lateral surface and/or between the counter-surface and the at least one lateral face are rounded.

In a preferred embodiment, the entire contact surface and the entire counter-surface of the membrane are arched.

Arching in the context of the present invention shall be understood to mean a curvature of surfaces, in the present invention the contact surface and the counter-surface.

According to the invention, the membrane is preferably singly arched, which in the case of a rectangular membrane means that two mutually opposing lateral faces are curved and the two other lateral faces are not curved.

In one embodiment, the membrane is designed as a shell, which is to say a membrane that is singly or doubly curved or arched.

In one embodiment, the membrane is arched so that it has the shape of a segment of a spherical shell, for example a hemispherical shell. In a further embodiment, the membrane is arched so that it has the shape of a cylindrical shell.

In a preferred embodiment, the radius of the arching corresponds to the radius of a bone to be treated, for example a long bone or a cranial bone.

In a preferred embodiment, the radius of the arching corresponds to the radius of a ridge of a jaw bone to be treated.

In a preferred embodiment, the arching has a radius of at least 5 mm. In a preferred embodiment, the arching has a radius of no more than 15 mm. In a preferred embodiment, the arching has a radius of at least 5 mm and of no more than 15 mm.

In an alternative embodiment of the invention, the respective edges that are formed by two lateral faces can be rounded.

In a preferred embodiment, the membrane has rounded edges.

A membrane that comprises a rectangular contact surface, a counter-surface and four rectangular lateral faces is preferred, wherein the contact surface and the counter-surface are arched, and wherein all the edges of the membrane are rounded.

In a likewise preferred alternative embodiment, the membrane is shaped and dimensioned so as to cover at least a portion of the surface of a jaw bone facing the teeth. A planar or an arched membrane can thus be provided, which in the planar state, which is to say in the flat state, is bent approximately in a horseshoe shape and has a length so that the membrane can cover at least a sub-region of an alveolar ridge. It is possible, in particular, for the membrane to cover the majority, for example up to 80%, of an alveolar ridge, or an entire alveolar ridge. A person skilled in the art, for example a dental technician, will be readily able to determine the size and shape of a membrane that is required to cover a desired alveolar ridge region. Membranes thus shaped can advantageously be used to treat wider bone defects, for example bone defects that cover several missing teeth, and even the entire alveolar ridge.

The shape and size of the membranes can be ready-made or individually adapted to the bone defect to be treated.

In a further embodiment, the membrane has at least one further arching, and more particularly several additional archings having smaller radii.

In a preferred embodiment, the membrane has bent edges. In a preferred embodiment, the membrane has at least two bent lateral faces.

In a preferred embodiment, the membrane has at least one perforation.

In a preferred embodiment, the membrane comprises titanium. In a preferred embodiment, the membrane is made of titanium. In a further embodiment, the membrane can also be made of a biodegradable material or comprise the same.

In a preferred embodiment, the membrane is sand-blasted. In a preferred embodiment, the contact surface of the membrane is sand-blasted.

In a preferred embodiment, the contact surface of the membrane is coated.

In a preferred embodiment, the edges of the membrane are covered with a non-woven fabric or a film.

In a preferred embodiment, in addition to the rounded region, the edges of the membrane are covered with a non-woven fabric or a film.

In a preferred embodiment, all the edges of the membrane between the contact surface and the at least one lateral face and between the counter-surface and the at least one lateral face are rounded and additionally are covered with a non-woven fabric or a film.

In an alternative embodiment, all the edges of the membrane between the contact surface and the at least one lateral face and between the counter-surface and the at least one lateral face are rounded and are not covered with a non-woven fabric or a film.

In an alternative embodiment, all the edges of the membrane between the contact surface and the at least one lateral face and between the counter-surface and the at least one lateral face are rounded and are not formed into beads or marginal ridges.

The membrane according to the invention can be intended for multiple uses or for single use. The membrane is preferably intended for single use because this is common practice with medical membranes, and the adhesive power of the surface of the membrane decreases upon contact with body fluid. The membrane according to the invention can be intended for single use in particular if the membrane was individually produced for a particular bone defect and/or if the membrane comprises biodegradable constituents, which break down on use.

In a preferred embodiment, the membrane according to the invention comprises at least one securing element. In a preferred embodiment, the securing element is located on the counter-surface of the membrane. The at least one securing element is used to secure the membrane to at least one actuating element. A securing element can be a perforation, an eyelet or an anchor point, for example. The at least one securing element is preferably a perforation, and more particularly a perforation for inserting a screw. If a perforation is used as the securing element, this can be a round hole, an elongated hole or an angled hole. The membrane can also comprise several differently shaped perforations. In an alternative embodiment, the securing element is used to secure a toothed rack. To this end, the securing element can be a perforation or a securing point, for example, such as a welding point or soldering point.

The present invention also relates to a membrane according to the invention, wherein the membrane is secured to at least one actuating element. In one embodiment according to the invention, the actuating element is a screw, a filament or a toothed rack. The actuating element is preferably a screw or a toothed rack. It is particularly preferred for the actuating element to be a toothed rack. In an alternative embodiment, the membrane is secured to several actuating elements, in particular screws.

In a preferred embodiment, the membrane according to the invention is a membrane for bone regeneration.

In an alternative embodiment, the membrane according to the invention is a membrane for periodontal regeneration. Periodontal regeneration shall be understood to mean regeneration of the periodontium, which is to say not only of the bone, but also of the periodontal ligament, the periodontal tissue, the gingiva and the papilla, for example by way of guided tissue regeneration (GTR). In a preferred embodiment, the membrane for periodontal regeneration has such small dimensions that the same can also be used in interdental spaces. In a preferred embodiment, the membrane for periodontal regeneration is very thin. In a preferred embodiment, the membrane for periodontal regeneration is shaped so that the membrane comprises at least one lobular extension or a segment that can be inserted into an interdental space. In a preferred embodiment, the membrane for periodontal regeneration is a single-piece, two-piece or multi-piece membrane. In a preferred embodiment, the membrane for periodontal regeneration comprises at least one securing element for securing a bone screw, for example at least one perforation.

The present invention also relates to a membrane according to the invention for use for callus distraction, in particular for reconstructing a jaw bone by way of distraction.

The present invention also relates to a membrane according to the invention for use for periodontal regeneration by way of distraction.

The present invention also relates to the use of a membrane according to the invention for callus distraction, in particular for reconstructing a jaw bone by way of distraction.

The present invention also relates to the use of a membrane according to the invention for use for periodontal regeneration by way of distraction.

The present invention also relates to a distraction device, comprising a membrane according to the invention, a fixation device and an actuating element, which connects the fixation device to the membrane.

The present invention also relates to a kit, including at least two of the membranes according to the invention. The present invention also relates to a kit, including a membrane according to the invention, a fixation device and an actuating element for connecting the fixation device to the membrane. The kit preferably includes directions for use.

The present invention also relates to a kit, including at least two of the distraction membranes according to the invention, in particular for producing a device according to the invention. The present invention also relates to a kit, including at least one distraction membrane according to the invention, a fixation device and an actuating element for connecting the fixation device to the membrane, in particular for producing a device according to the invention. The kit preferably includes directions for use.

The present invention also relates to a method for callus distraction, in particular for reconstructing a jaw bone by way of distraction, wherein a membrane according to the invention is applied to a bone segment to be regenerated and tensile stress is applied to this membrane by way of a distraction device. Methods in which the membrane according to the invention can be used are known from WO 01/91663 A1 or U.S. Pat. No. 5,980,252, for example, the content of which describes the options for using the membranes according to the invention based on an example of membranes from the prior art and is hereby included in the present application. Without being bound to theory, in particular, a distance of approximately 1.5 mm between the membrane and the bone is advantageous at the start of the procedure for such distraction methods.

BRIEF DESCRIPTION OF THE DRAWINGS

The invention will be described in greater detail hereafter based on the drawings. In the drawings.

DETAILED DESCRIPTION OF THE INVENTION

Figure 1A:
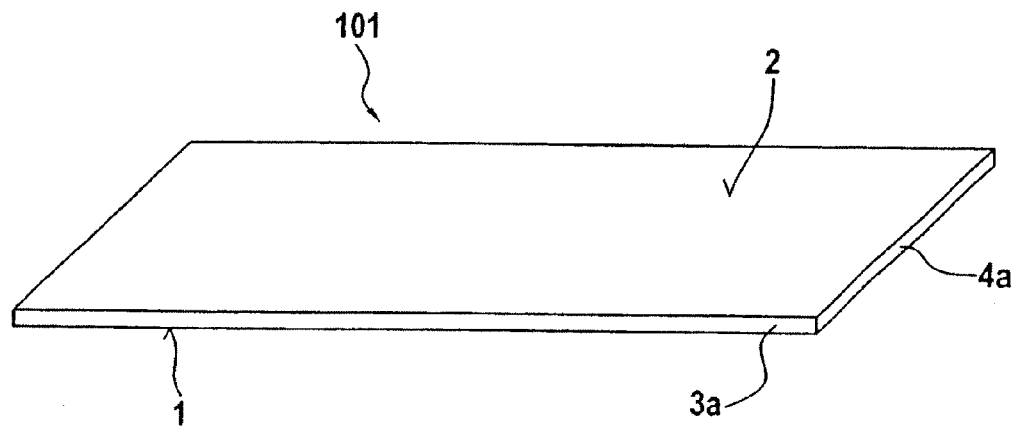
FIG. 1a shows a membrane of the prior art.

FIG. 1a shows a distraction membrane 101 from the prior art. The distraction membrane 101 has a contact surface 1, which is not visible here, and a counter-surface 2. Of the four lateral faces, the faces 3a and 4a, which adjoin each other, can be seen. Such a membrane can be used as described in WO 01/91663 A1 and U.S. Pat. No. 5,980,252, wherein the contact surface 1 faces a bone and the membrane is moved away, for example pulled away, from the bone at a particular rate, for example approximately 0.5 mm to 2 mm per day, and in particular approximately 1 mm per day, using a distraction device.

Figure 1B:
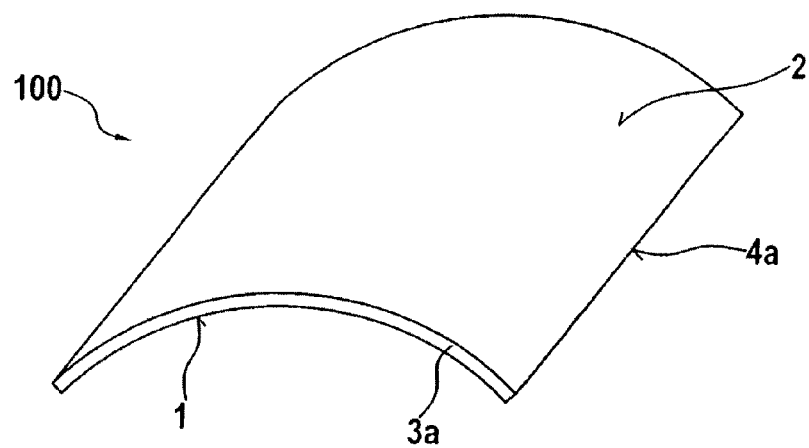
FIG. 1b shows a membrane according to the invention, comprising a rectangular contact surface.

FIG. 1b shows a membrane according to the invention that is arched. The membrane 100 has a contact surface 1 and a counter-surface 2. In addition, the membrane has four lateral faces 3a, 3b, 4a and 4b, of which only the two mutually adjoining lateral faces 3a and 4a can be seen. In a preferred embodiment, the membrane is singly arched, as shown in FIG. 1b. According to the invention, the contact surface 1 is concavely curved and the counter-surface 2 is convexly curved. With a single curvature of the shown membrane 100 having rectangular faces, two mutually opposing lateral faces 3a and 3b are curved and the other two mutually opposing lateral faces 4a and 4b are not curved.

The arched geometry of the membrane advantageously results in greater stability of the membrane against warping. This makes it possible to use distraction membranes having a very small membrane height, which is to say membrane thickness. This is advantageous when using such a membrane for callus distraction in the jaw region, because here the membrane is placed under the mucous membrane, and membranes having a large height result in tension in the mucosal flaps, which can cause ischemia associated with tissue necroses. This can also result in membrane exposure, as a result of which a membrane that is subject to bacterial colonization has to be removed. The arched geometry of a membrane according to the invention now allows stable membranes having a low height to be used, so that tension on the mucous membrane can be avoided.

The membrane preferably has a height of no more than 1 mm, and more particularly of no more than 0.5 mm.

In a preferred embodiment, the membrane 100 has a length of at least 5 mm and no more than 120 mm and a width of at least 5 mm and no more than 120 mm. For example, the membrane can have a length of approximately 20 mm and a width of approximately 10 mm. The length and width information applies to the membrane in the non-arched state. The membrane can in particular have approximately the width of an alveolar ridge and the length of a portion of the alveolar ridge or of the entire alveolar ridge.

A wide variety of suitable materials for distraction membranes are known to a person skilled in the art. The membrane is preferably made of a biocompatible material. The membrane is preferably made of a metal, in particular titanium. Membranes made of metals such as titanium have the advantage that they are very stable, despite having a small height.

However, alternatively, the membrane can also be made of a biocompatible plastic material.

The plastic material is preferably a bioresorbable plastic material. These have the advantage that they do not have to be removed after the distraction.

Of course, the membrane can also have rounded edges.

Figure 1C:
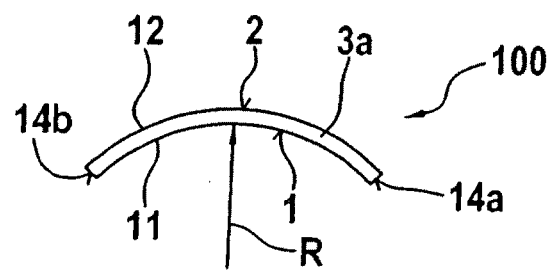
FIG. 1c shows a side view of the membrane of FIG. 1b.

FIG. 1c shows a side view of the arched membrane 100 according to the invention. Shown is the curved lateral face 3a, the edge 11 of which adjoins the concave contact surface 1 and the curved edge 12 of which adjoins the convex counter-surface 2. The edges 14a and 14b of the lateral face 3a adjoin the lateral faces 4a and 4b.

The membrane 100 is arched evenly over the entire contact surface 1. However, it is also possible that only sub-regions of the contact surface 1 are arched, for example only the center third of the edge 11 is arched. The radius R of the arching can also be different in various regions of the contact surface. According to the invention, the radius R of the arching of the contact surface 1 is preferably adapted to the natural shape of a bone, for example the shape of a jaw. The radius R of the arching of the contact surface is preferably at least 5 mm and no more than 15 mm, particularly preferably at least 5 mm and no more than 12 mm, and in particular at least 6 mm and no more than 10 mm. The radius R of the arching of the contact surface 1 is preferably at least 5 mm, particularly preferably at least 6 mm. The radius R of the arching of the contact surface 1 is preferably no more than 15 mm, particularly preferably 12 mm, and in particular no more than 10 mm. The radius R of the arching of the contact surface 1 is preferably approximately 6 to 7 mm.

An arched membrane according to the invention thus not only has the advantage of increased stability with a low height, but such a membrane is advantageously also shaped so that the arching is consistent with the anatomical and physiological conditions of the bone to be regenerated. This allows the bone to be regenerated over the entire contact surface of the membrane because this membrane, during distraction, has approximately the same distance from the regenerating bone at every point.

Of course, the membrane can also have rounded edges.

Figure 1D:
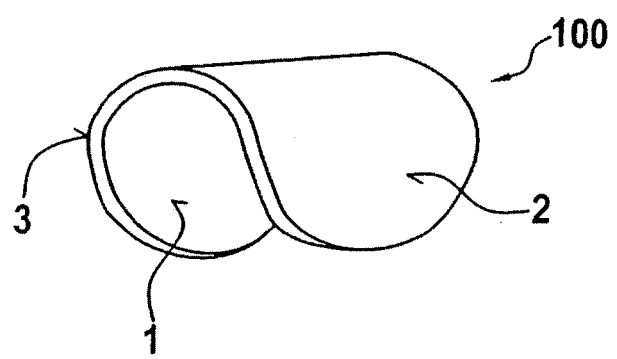
FIG. 1d shows a membrane according to the invention, comprising a circular contact surface.

FIG. 1d shows an arched membrane 100 according to the invention, in which the contact surface 1 and the counter-surface 2 are not rectangular, but circular. Such a membrane thus has only one lateral face 3.

Of course, the membrane can also have rounded edges.

Figure 2A:
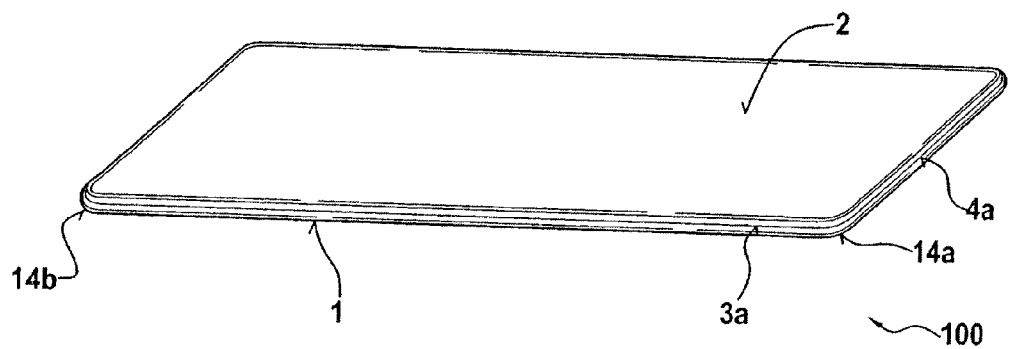
FIG. 2a shows a membrane according to the invention, comprising rounded edges.
Figure 2B:
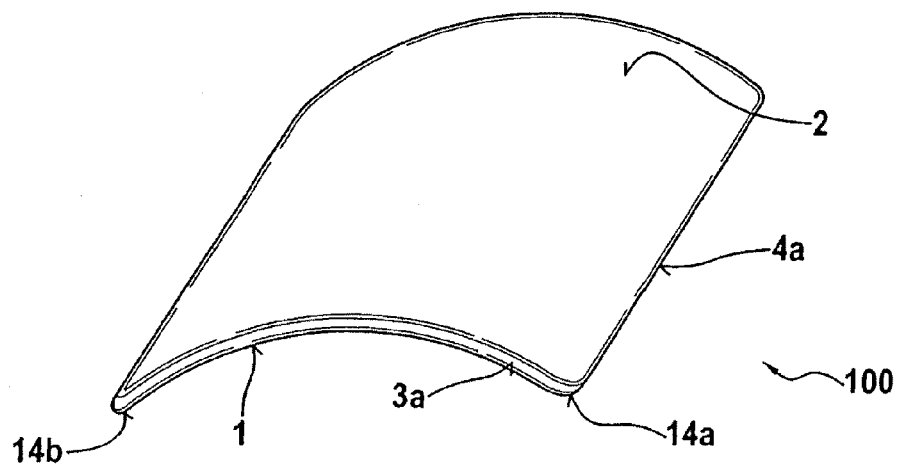
FIG. 2b shows an arched membrane having rounded edges.

FIG. 2a shows a planar membrane 100 according to the invention, having rounded edges. A membrane on which all edges are rounded is preferred. However, it is also possible that only the edges between the contact surface 1 and the at least one lateral face 3a, 4a and/or the edges between the counter-surface 2 and the at least one lateral face 3a, 4a are rounded. Because the lateral faces 3a, 4a are very narrow due to the low height of the membrane, it is also possible for the edges between the contact surface 1 of the membrane 100 and the at least one lateral face 3a, 4a of the membrane, and between the counter-surface 2 of the membrane 100 and the at least one lateral face 3a, 4a of the membrane 100, to be rounded so that the two rounded regions transition into each other. It is thus possible for the at least one lateral face 3a, 4a to be rounded. This is shown in FIG. 2b. The edges 14a, 14b between the individual lateral faces 3a, 4a are also preferably rounded. Preferably not only the edges, but also the corners of the membrane are rounded.

Rounding the edges of a membrane advantageously prevents the edges from injuring the surrounding tissue, for example by cutting or crushing the tissue or fine vessels and capillaries, when the membrane is moved during distraction. Because of the rounded edges and/or corners, a membrane according to the invention can advantageously slide past the adjacent tissue without damaging the same. The rounded edges advantageously make it easier to adapt the mucous membrane over the membrane.

FIG. 2b shows an arched membrane 100 having rounded edges 4a, 4b.

The combination of the arching according to the invention and rounding of the edges according to the invention advantageously results in a membrane that protects the adjacent tissue particularly well during the distraction because the membrane edges do not compress the fine vessels and capillaries of the adjacent tissue, which are very important for providing tissue nutrients to the mucous membrane covering the membrane. This prevents premature membrane exposure.

During the distraction of the membrane, the rounded edges and the arching of the membrane advantageously also prevent a sudden increase in pressure in the surrounding vessels, especially the smaller vessels. Preventing such a sudden rise in pressure is beneficial for wound healing.

According to a further embodiment, the edges can additionally be covered with a non-woven fabric or a film. The non-woven fabric or the film can be bioresorbable or non-bioresorbable.

Covering the edges with a non-woven fabric or a film offers additional protection for the adjacent tissue, in particular if the membrane is made of a very hard material, such as titanium for example.

Figure 2C:
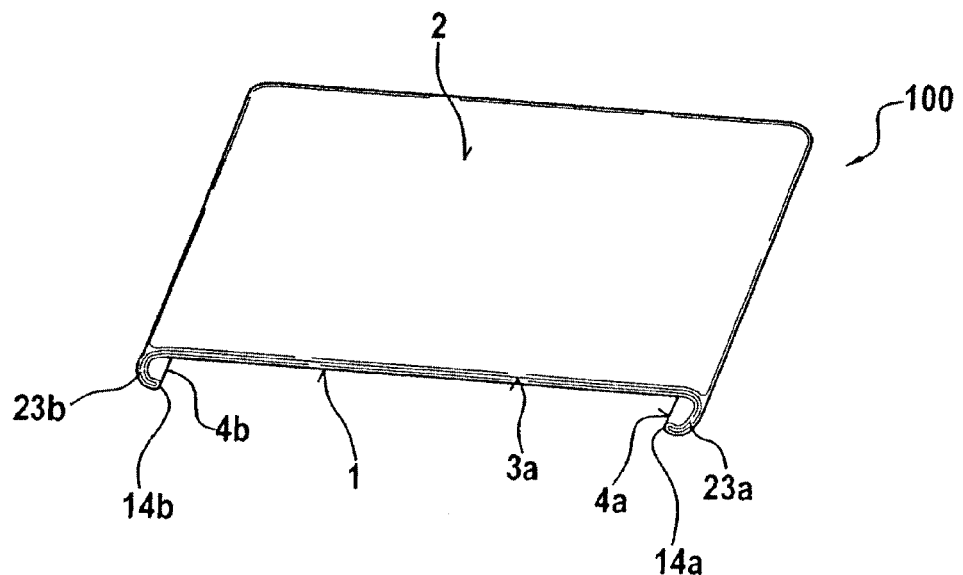
FIG. 2c shows a membrane having bent edge regions.

FIG. 2c shows a planar membrane 100 having rounded edges 14a, 14b, wherein the lateral faces 4a, 4b are also bent toward the contact surface 1. The membrane is thus bent in at least two outer regions 23a, 23b of the contact surface 1 and of the counter-surface 2, in particular it is bent toward the contact surface 1.

Bending the at least one lateral face 4a, 4b of the membrane also protects the adjacent tissue when the membrane is used because the tissue is seated against the bend, and not against a sharp edge. The edges therefore do not necessarily have to be rounded when the lateral faces are bent.

Because, during use, the membrane 100 is typically moved in the direction of the counter-surface 2, the lateral faces 4a, 4b are preferably bent in the direction of the contact surface 1.

The lateral faces are preferably bent very significantly, and in particular they are bent so significantly that the edges do not come in contact with the tissue. For example, the lateral faces can be rolled in, and in particular can be rolled in with a very small radius to form what one may call "beads".

As an alternative, the edges can be bent at an angle of up to 90 degrees relative to the adjoining membrane surface.

Of course, the bent lateral faces can also be combined with rounded edges.

Figure 2D:
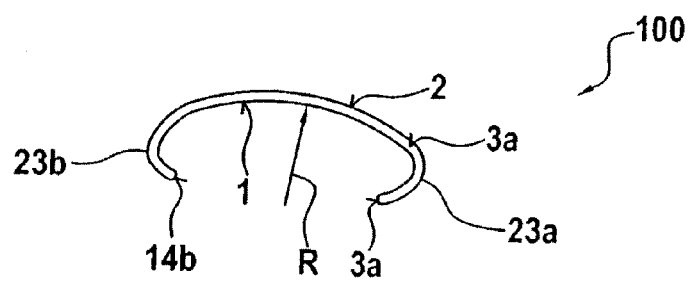
FIG. 2d shows an arched membrane having bent edge regions and rounded edges.

FIG. 2d shows an arched membrane 100 having rounded edges 14a, 14b, wherein the lateral faces 4a, 4b are also bent toward the contact surface 1. The bends 23a, 23b of the edges 4a, 4b can be seen here as amplified arches of the basic arching of the membrane 100. In a preferred embodiment, the bends thus have a radius that is smaller than the radius R of the basic arching of the membrane.

Figure 3:
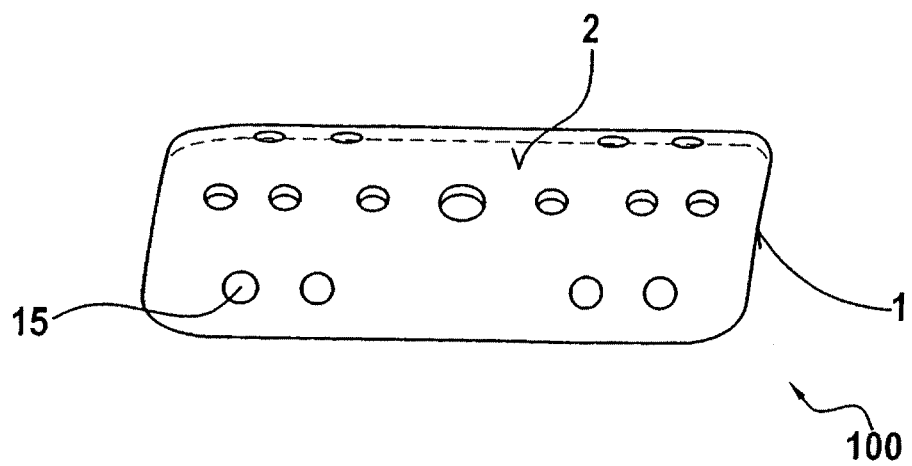
FIG. 3 shows an arched membrane having perforations.

FIG. 3 shows an embodiment of an arched membrane 100, wherein the membrane 100 is perforated so that the contact surface 1 and the counter-surface 2 are connected to each other by at least one hole 15, and more particularly by a plurality of holes, which can be distributed in particular over the entirety of the surfaces. In a preferred embodiment, the perforation holes have a diameter at least approximately 0.3 mm and no more than approximately 1.3 mm.

Perforation holes, and perforation holes having a diameter of approximately 1 mm in particular, allow capillaries to grow through the membrane, whereby excellent blood circulation and immune defense are ensured in the region of the newly formed bone. The perforations allow good blood flow through the mucous membrane covering the membrane and through the regenerated tissue between the membrane and the bone.

The number of perforation holes preferably varies depending on the size of the membrane. For example, a membrane having a length of approximately 20 mm and a width of approximately 10 mm can have approximately 10 to 20 perforation holes. Such a ratio of the number of perforation holes to the membrane surface provides an optimum balance between the total hole surface promoting blood circulation and the adhesion surface for osteoblasts adhering to the membrane during the distraction process.

Figure 4A:
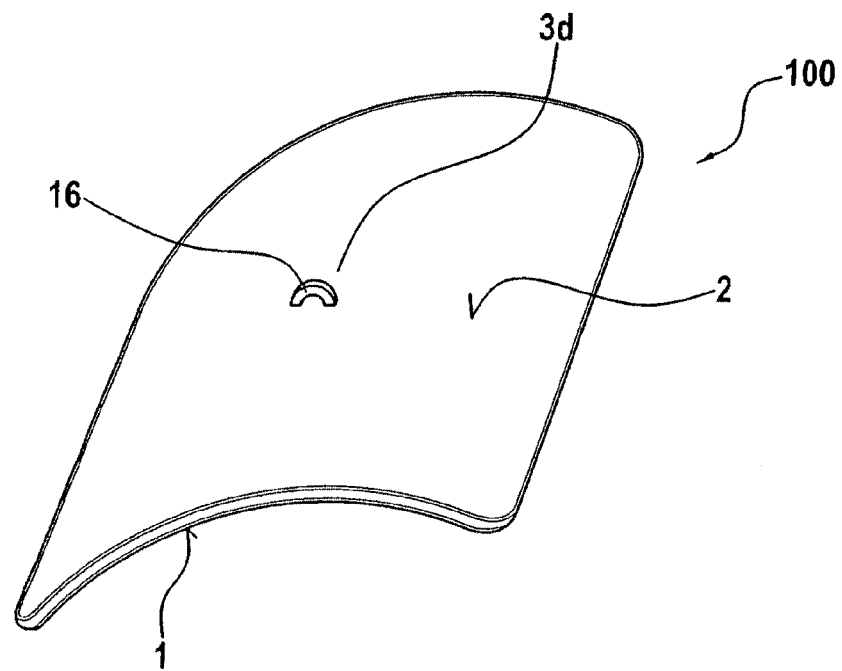
FIG. 4a shows a membrane comprising an eyelet as a securing element.

FIG. 4a shows a membrane 100 that is arched according to the invention, comprising an eyelet 16 as a securing element. The eyelet 16 is located on the counter-side 2 of the membrane 100. A distraction device can also be attached to the eyelet 16, for example by way of a wire. By virtue of the distraction device, the membrane 100 can be used for callus distraction in the defect region of a bone by being pulled away from a bone defect at an adapted rate of approximately 1 mm per day.

Figure 4B:
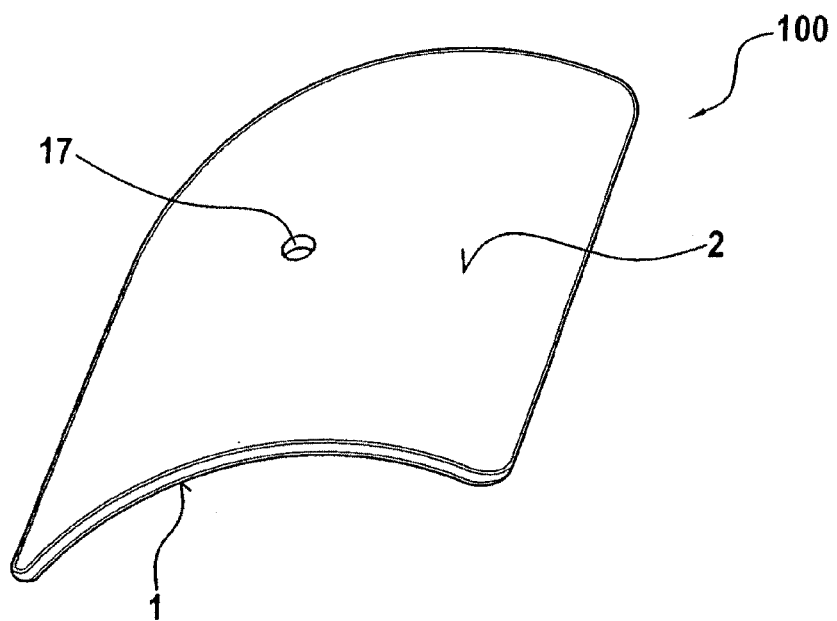
FIG. 4b shows a membrane comprising a hole as a securing element.

FIG. 4b shows a membrane 100 that is arched according to the invention, comprising a hole 17 as a securing element. For example, a toothed rack of a distraction device can be inserted into the hole 17 and secured to the membrane 100, for example by way of welding, in particular laser welding, soldering or gluing.

Figure 5:
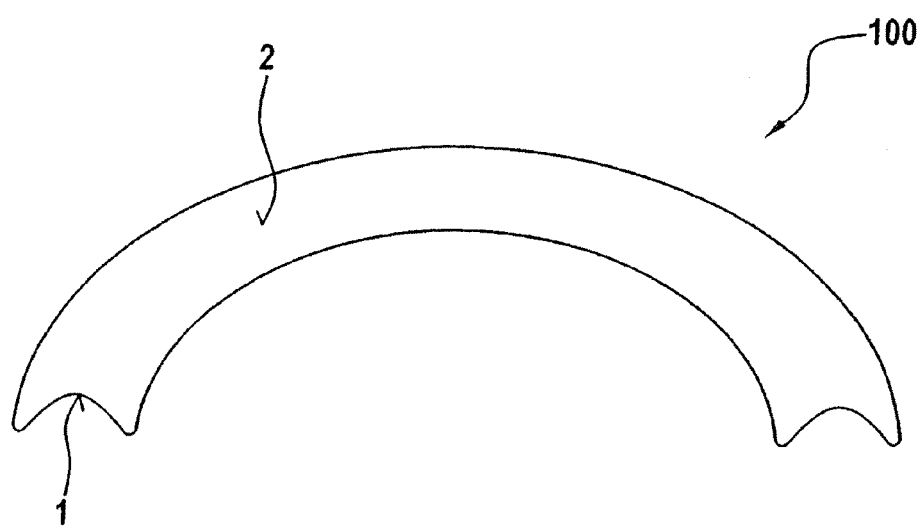
FIG. 5 shows a horseshoe-shaped membrane for treating large-surface-area jaw defects.

FIG. 5 shows a preferred horseshoe-shaped embodiment of the membrane 100 for treating large-surface-area jaw bone defects.

The membrane 100 shown, having the contact surface 1 and the counter-surface 2, can be used, for example, if all the teeth, or a large number of teeth next to each other, of a jaw are missing and the jaw bone has to be regenerated so as to be able to perform implants. If not all the teeth of the jaw are missing, but only a large number of teeth that are located next to each other, the membrane 100 can be shortened and adapted accordingly.

Figure 6A:
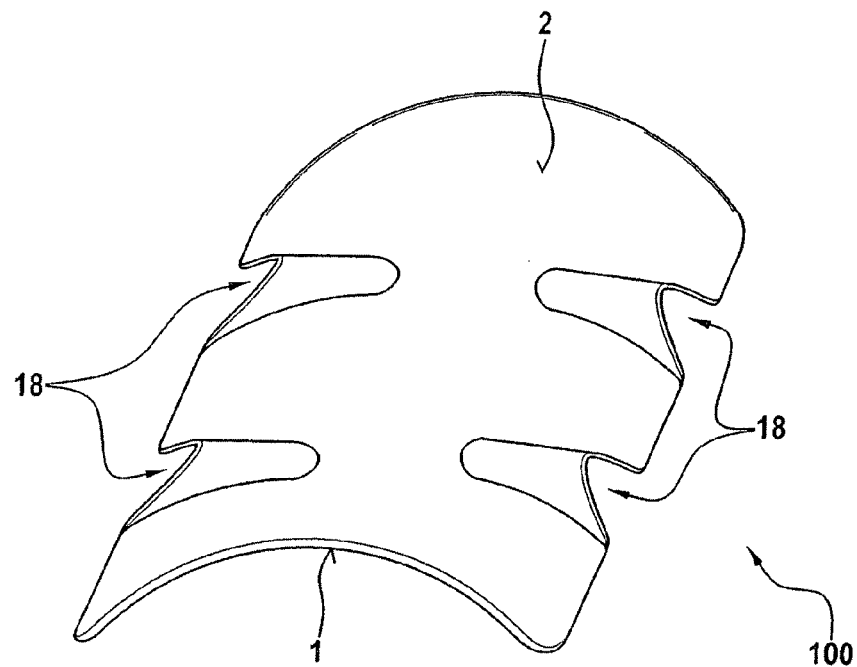
FIG. 6a shows a membrane comprising further archings for interdental papilla.

FIG. 6a shows an alternative embodiment of the membrane 100 according to the invention, comprising the contact surface 1 and the counter-surface 2, in which additional archings 18 for the interdental papilla are provided. These additional archings 18 are adapted to the shape of the jaw bone forming the interdental papilla. The jaw bone is raised between two adjacent teeth in a region of approximately 2 mm, whereby the periodontium is higher there than in the region of the teeth.

The additional archings can be provided so as to preserve this raised bone area even after bone regeneration by way of distraction. In order for the archings to follow the shape of the interdental papilla, these preferably have a radius of 0.5 mm to 1.5 mm, in particular approximately 1 mm, and are located offset by an angle of approximately 90 degrees relative to the first arching according to the invention. In a planar membrane, these archings are located along the longitudinal sides of the membrane running parallel to the alveolar ridge. A person skilled in the art, for example a dental technician, will be able to determine without great effort the dimensioning and positioning of additional archings that follow the shape of interdental papilla.

Figure 6B:
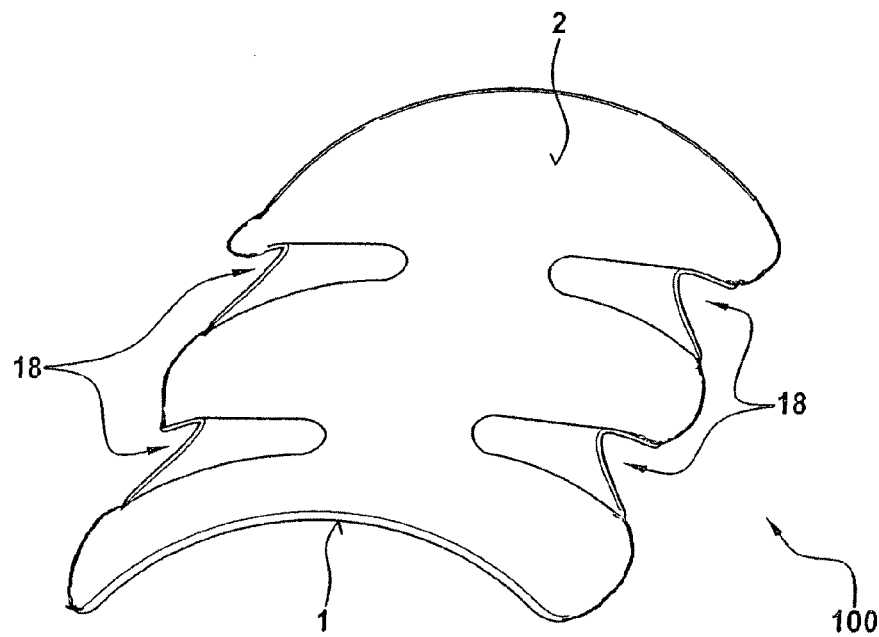
FIG. 6b is an alternative embodiment of the membrane comprising further archings for interdental papilla.

FIG. 6b shows an alternative embodiment of the membrane 100 of FIG. 6a. In this embodiment, the membrane surfaces 1, 2 are extended downward further between the additional archings 18, so that the alveolar ridge can also be covered laterally by the membrane.

Figure 7:
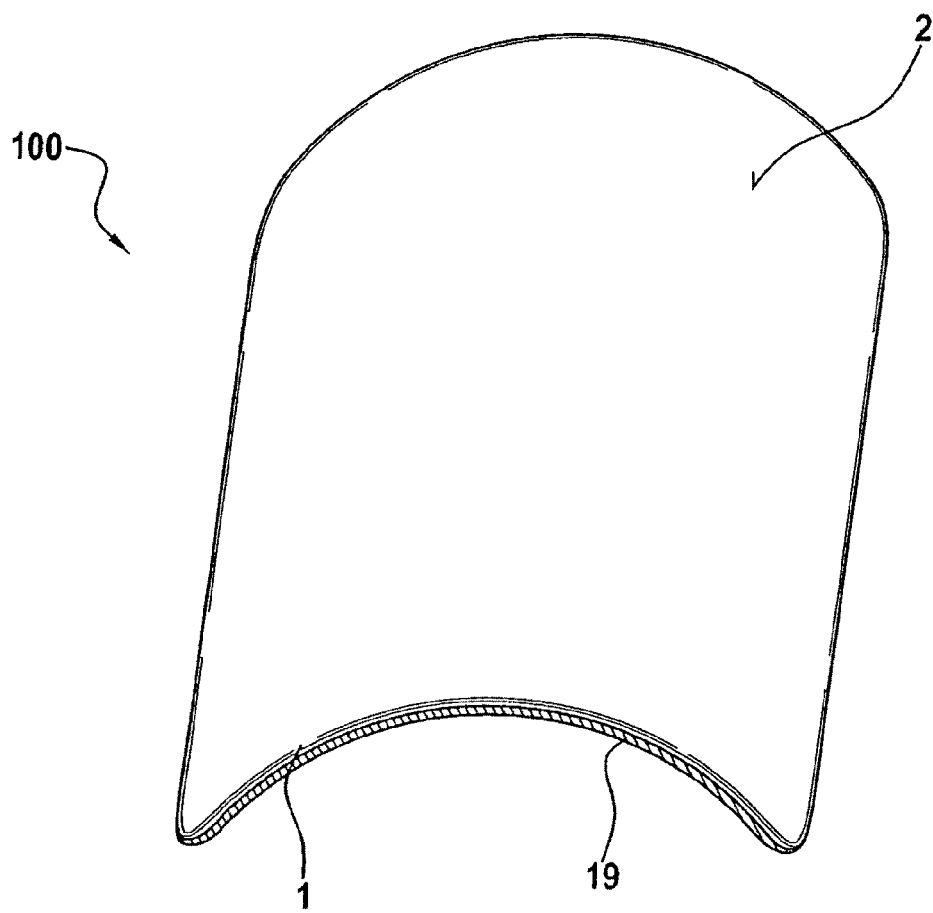
FIG. 7 shows a membrane, the contact surface of which is coated.

FIG. 7 shows an alternative embodiment of the membrane 100, in which the contact surface 1 of the membrane 100 is covered by a coating 19.

In a preferred embodiment, the contact surface 1 of the membrane 100 is coated with hydroxylapatite. In a further preferred embodiment, the contact surface 1 of the membrane 100 is coated with a bone substitute material, in particular a natural or synthetic bone substitute material.

The bone substitute material is preferably a natural bone substitute material, for example made of the mineral component of bones, in particular autogenous, allogenic or xenogenic bone, for example animal bones, and bovine bones in particular. A suitable bone substitute material is Bio-Oss®, which is available from Geistlich, for example.

In a further preferred embodiment, the contact surface of the membrane is coated with a bone substitute material and a biodegradable glue, in particular a fibrin glue. The bone substitute material is preferably joined to the contact surface of the membrane by way of the fibrin glue. Such a coating advantageously allows the newly generated bone tissue to adhere to the membrane before and during the distraction because the bone tissue can adhere well to the biological substitute material. In addition, such a coating allows for easy detachment, in particular even autonomous detachment of the membrane from the newly formed bone after completion of the distraction, because the fibrin glue is biodegradable, and thus is biologically degraded and decomposed during, and in particular after, the distraction. The coating made of bone substitute material thus detaches from the contact surface of the membrane. The membrane can be removed without having to be separated further from the bone, and the bone substitute material can remain in the restored bone defect.

Figure 8:
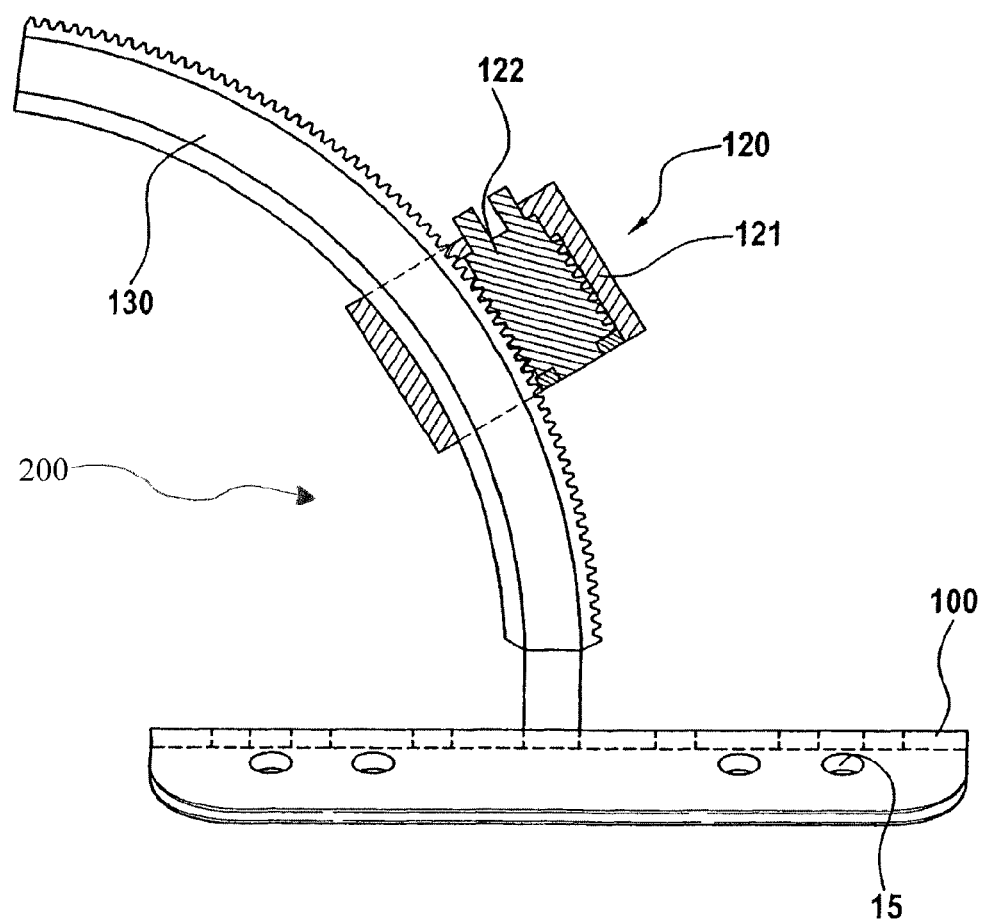
FIG. 8 shows a distraction device, comprising a membrane, a fixation device, and an actuating element connecting the fixation device to the membrane in the form of a toothed rack.

FIG. 8 shows a distraction device 200, comprising an arched membrane 100 having perforations 15, a fixation device 120, and an actuating element in the form of a toothed rack 130 that connects the fixation device 120 to the membrane 100. The distraction membrane 100 is secured to one end of the toothed rack 130. The toothed rack 130 is curved, but can also be straight. The fixation device 120 comprises a gear system, in particular a self-locking gear system, for moving the toothed rack, wherein the gear system can be disposed in a stationary manner in the region of the bone to be regenerated, in particular in the oral cavity. The gear system comprises a housing 121 having a passage and a threaded body 122, wherein the toothed rack 130 is inserted in the longitudinal extension through the passage at least substantially without play through the housing 121, and wherein the threaded body 122 is rotatably mounted in the housing 121 so that the threaded body 122 and the toothed rack 130 are operatively engaged with each other. The gear system 120 can be disposed in a stationary manner in the region of a bone to be regenerated, in particular in the oral cavity, by way of additional elements of the fixation device 120, for example brackets or bridges.

Distraction devices for regenerating bone, comprising a distraction membrane and an actuating element actuating the distraction membrane, wherein the actuating element is designed as a toothed rack, are disclosed in a patent application by the same inventor (published as WO 2012-076160-A, U.S. national stage is Jordan and Hamburg, "Universal Distraction Device for Bone Regeneration"), which has the same filing date as the present application, the disclosure of which is hereby incorporated herein by reference.

Figure 9A:
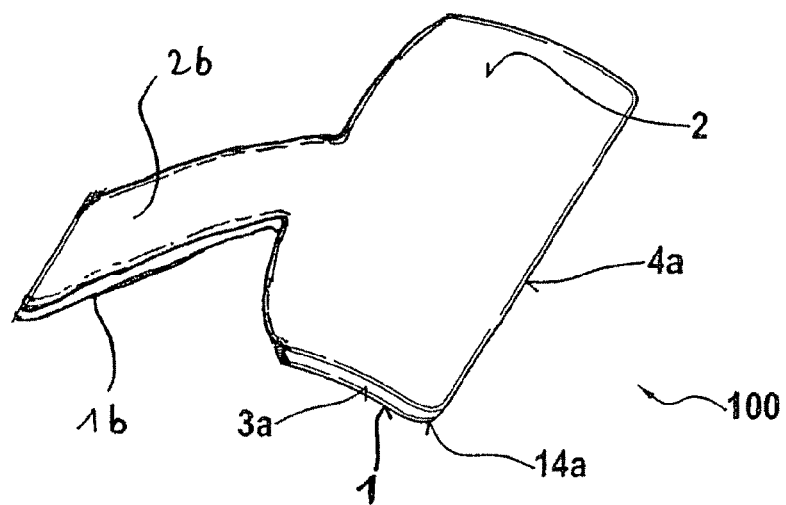
FIG. 9a shows a membrane for periodontal regeneration, comprising a segment for insertion into an interdental space.
Figure 9B:
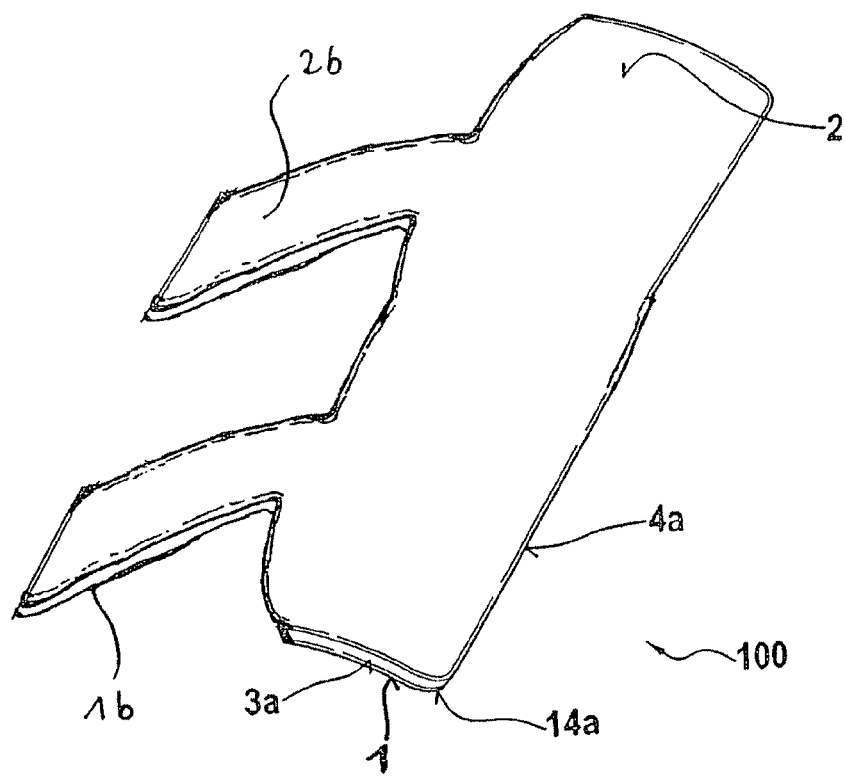
FIG. 9b shows a membrane for periodontal regeneration, comprising two segments for insertion into an interdental space.

FIGS. 9a and 9b show preferred embodiments of an arched membrane 100 for periodontal regeneration. The membranes 100 are very thin and have rounded edges 3a, 4a. The membranes comprise segments having the surfaces 1b and 2b, which can be inserted into the interdental spaces. The membrane in FIG. 9a has one such segment, and the membrane in FIG. 9b has two such segments. Of course, it is also possible to provide more than two, for example three or four, segments. The membrane can be inserted both from the vestibular side and from the lingual side, or simultaneously from both sides. Such a membrane is preferably used together with bone screws.

It is a matter of course that the preferred embodiments shown in FIGS. 1 to 9 can be arbitrarily combined with each other.

The present invention will be described in greater detail based on the following example and FIG. 10.

Figure 10:
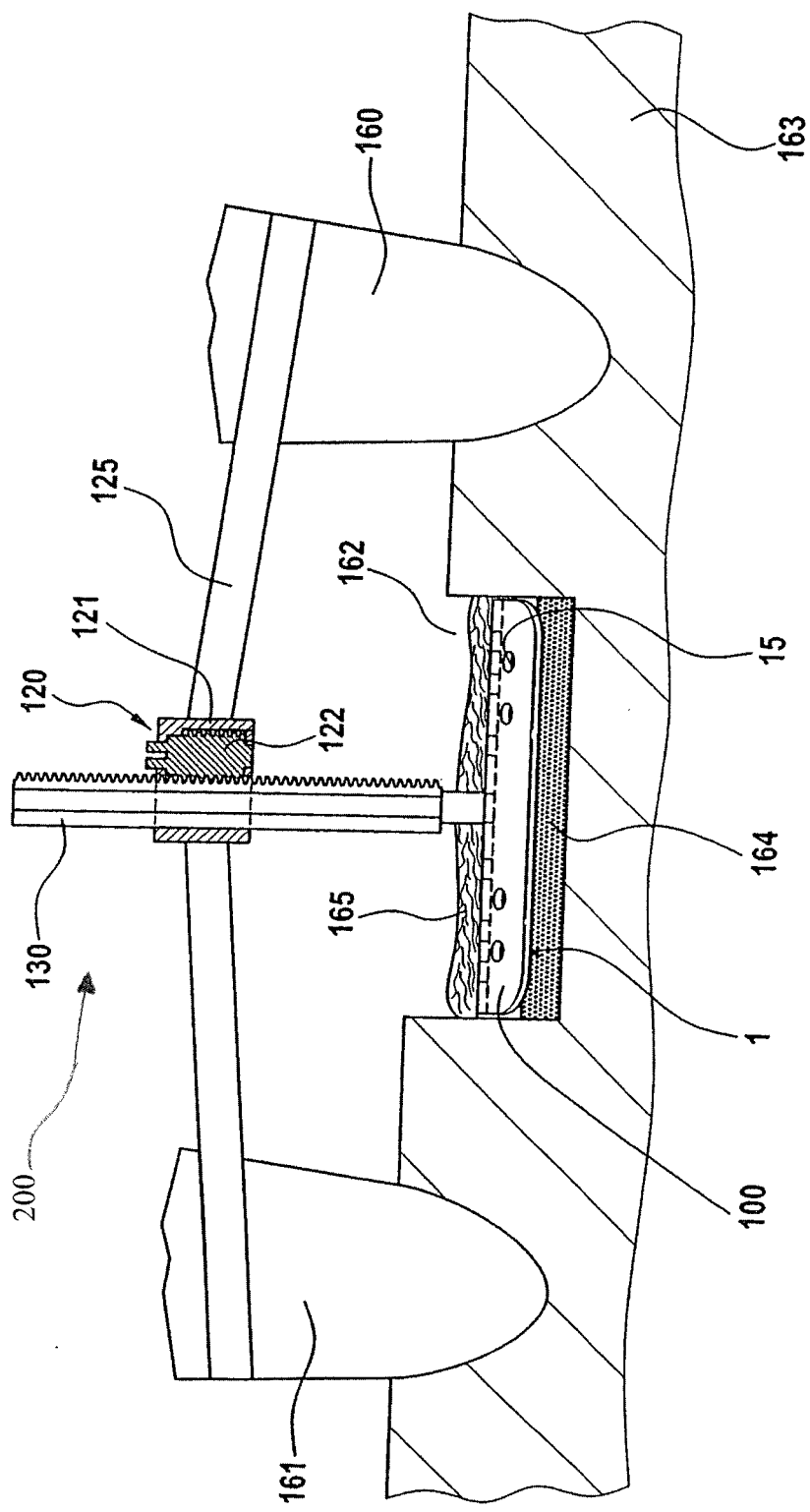
FIG. 10 shows a distraction device in an oral cavity.

FIG. 10 shows a distraction device 200 comprising an arched membrane 100 according to the invention. The membrane is connected to a gear system 120 by way of a toothed rack 130. The gear system 120 is laminated into a bridge 125, which is secured to two teeth 160, 161. A gap having a bone defect 162 of the arched jaw bone 163 is located between the teeth 160, 161. The contact surface 1 of the membrane 100 is seated against the jaw bone in the bone defect. Because the membrane 100 approximately follows the arching of the jaw bone 163, the contact surface 1 is seated thereon evenly. Without being bound to theory, in particular, a distance of approximately 1.5 mm between the membrane 100 and the bone 163 is advantageous. A coagel 164 has formed between the jaw bone 163 and the membrane 100, with osteoblasts also being present in this coagel. These osteoblasts can adhere to the contact surface 1 of the membrane 100. If the threaded body 122 in the housing 121 of the gear system 120 is now turned using a screwdriver or the like, the toothed rack 130, together with the membrane 100, moves upward. The threaded body 122 can be turned so that the membrane 100 moves away from the jaw bone 163 at a rate of approximately 1 mm per day. For example, the threaded body 122 can be turned once a day by a particular revolution, or twice a day by half this revolution. By lifting the membrane, biomechanical stimuli are applied to the osteoblasts adhering to the contact surface 1 in the coagel 164, resulting in osteogenesis. Using the perforations 15 in the membrane 100, the coagel 164 and the bone callus having formed therein are provided with sufficient circulation via the tissue 165 located over the membrane 100. Because of the arching of the membrane 100, the bone defect 162 of the jaw bone 163 is thus filled with new bone substance, so that the filled-in bone defect has the convexly shaped arching of the jaw bone 163.

The invention claimed is:

1. A callus distraction membrane, comprising:
   a contact surface as a first face of the callus distraction membrane adapted for contacting a callus of bone to promote osteogenesis;
   a counter-surface opposite the contact surface as a second face of the callus distraction membrane; and
   a peripheral edge surface extending along an entire periphery of the callus distraction membrane, the peripheral edge surface spanning between the contact surface and the counter-surface everywhere along said entire periphery; and
   wherein the peripheral edge surface is rounded in a transverse direction from the contact surface to the counter-surface everywhere along said entire periphery;
   wherein along the periphery are a plurality of corners that are rounded along a peripheral direction; and
   wherein at least a sub-region of the contact surface is arched and wherein a corresponding sub-region of the counter-surface is arched.

2. The membrane according to claim 1, wherein the arching has a radius of at least 5 mm and of no more than 15 mm.

3. The membrane according to claim 1, wherein the membrane has at least one perforation.

4. The membrane according to claim 1, wherein the membrane comprises titanium.

5. The membrane according to claim 1, wherein the edges of the membrane are covered with a non-woven fabric or a film.

6. The membrane according to claim 1 in combination with at least one actuating element, wherein the membrane is secured to the at least one actuating element.

7. The membrane according to claim 1, wherein the membrane is shaped and dimensioned so as to cover at least a portion of a surface of a jaw bone facing teeth.

8. A method of bone distraction comprising:
   covering at least a portion of a surface of a bone with a callus distraction membrane comprising:
   a contact surface as a first face of the callus distraction membrane adapted for contacting a callus of bone to promote osteogenesis;
   a counter-surface opposite the contact surface as a second face of the callus distraction membrane; and
   a peripheral edge surface extending along an entire periphery of the callus distraction membrane, the peripheral edge surface spanning between the contact surface and the counter-surface everywhere along said entire periphery; and
   wherein the peripheral edge surface is rounded in a transverse direction from the contact surface to the counter-surface everywhere along said entire periphery;
   wherein along the periphery are a plurality of corners that are rounded along a peripheral direction; and
   wherein at least a sub-region of the contact surface is arched and wherein a corresponding sub-region of the counter-surface is arched.

9. A distraction device, comprising the membrane according to claim 1, a fixation device, and an actuating element connecting the fixation device to the membrane.

10. A kit, comprising the membrane according to claim 1, a fixation device, and an actuating element for connecting the fixation device to the membrane.

11. The membrane according to claim 1, wherein the membrane is shaped and dimensioned for bone distraction in a jaw region.

12. The membrane according to claim 1, wherein the membrane consists of titanium.

13. The method according to claim 8, wherein the bone is a jaw bone.

14. A method of bone distraction, comprising:
   covering at least a portion of a surface of a jaw bone facing teeth with a callus distraction membrane comprising:
   a contact surface as a first face of the callus distraction membrane adapted for contacting a callus of bone to promote osteogenesis;
   a counter-surface opposite the contact surface as a second face of the callus distraction membrane; and
   a peripheral edge surface extending along an entire periphery of the callus distraction membrane, the peripheral edge surface spanning between the contact surface and the counter-surface everywhere along said entire periphery; and
   wherein the peripheral edge surface is rounded in a transverse direction from the contact surface to the counter-surface everywhere along said entire periphery;
   wherein along the periphery are a plurality of corners that are rounded along a peripheral direction; and
   wherein at least a sub-region of the contact surface is arched and wherein a corresponding sub-region of the counter-surface is arched.

15. The combination according to claim 6, of the membrane and the at least one actuating element, wherein the at least one actuating element comprises a screw, a string or a toothed rack.

16. The method of claim 8, further comprising connecting a fixation device to the distraction membrane with an actuating element.

17. The method of claim 8, wherein at least said sub-region of the contact surface and said sub-region of the counter-surface are arched to have a radius of at least 5 mm and of no more than 15 mm.

18. The method of claim 8, wherein the membrane has at least one perforation.

19. The method of claim 8, wherein the membrane comprises titanium.

20. The method of claim 8, wherein the edges of the membrane are covered with a non-woven fabric or a film.

21. The method of claim 8, further comprising securing the membrane to at least one actuating element.

22. The method of claim 8, wherein the membrane is shaped and dimensioned so as to cover at least a portion of a surface of a jaw bone facing teeth.

23. The method of claim 8, wherein the membrane is shaped and dimensioned for bone distraction in a jaw region.

24. The method of claim 8, wherein the membrane consists of titanium.

* * * * *